United States Patent
Ananthan et al.

(10) Patent No.: US 10,743,923 B2
(45) Date of Patent: Aug. 18, 2020

(54) FIXATION SYSTEM AND METHOD FOR HOFFA FRACTURES

(71) Applicant: Acumed LLC, Hillsboro, OR (US)

(72) Inventors: Bharadwaj Ananthan, Portland, OR (US); Thomas R. Lyon, Brooklyn, NY (US); Amir Meir Matityahu, Los Altos, CA (US); Andrew Howard Schmidt, Orono, MN (US)

(73) Assignee: Acumed LLC, Hillsboro, OR (US)

( * ) Notice: Subject to any disclaimer, the term of this patent is extended or adjusted under 35 U.S.C. 154(b) by 275 days.

(21) Appl. No.: 15/723,682

(22) Filed: Oct. 3, 2017

(65) Prior Publication Data

US 2018/0092676 A1 Apr. 5, 2018

Related U.S. Application Data

(60) Provisional application No. 62/404,115, filed on Oct. 4, 2016.

(51) Int. Cl.
*A61B 17/58* (2006.01)
*A61B 17/80* (2006.01)
*A61B 17/88* (2006.01)

(52) U.S. Cl.
CPC ...... *A61B 17/8057* (2013.01); *A61B 17/8004* (2013.01); *A61B 17/8061* (2013.01)

(58) Field of Classification Search
CPC ............ A61B 17/8057; A61B 17/8004; A61B 17/8061; A61B 17/80; A61B 17/8019; A61B 17/8023

(Continued)

(56) References Cited

U.S. PATENT DOCUMENTS

| 4,473,069 A | 9/1984 | Kolmert |
| 5,681,313 A | 10/1997 | Diez |

(Continued)

FOREIGN PATENT DOCUMENTS

| AU | 761199 B2 | 12/2000 |
| CN | 103654930 A | 3/2014 |

(Continued)

OTHER PUBLICATIONS

Thomas, Shane, Authorized Officer, International Searching Authority / US Commissioner for Patents, "International Search Report" in connection with related International Application No. PCT/US2017/054901, dated Dec. 5, 2017, 2 pgs.

(Continued)

*Primary Examiner* — Jessica Weiss
(74) *Attorney, Agent, or Firm* — K&L Gates LLP

(57) ABSTRACT

System and method for fixing a distal femur having a Hoffa fracture. The system may comprise a main plate, an outrigger plate, and a coupling member that mounts the outrigger plate to the main plate. In an exemplary method, an elongated body portion of the main plate may be secured to a shaft region of the distal femur, and a wider head portion of the main plate may be secured to an end region of the distal femur. The outrigger plate may be mounted on the head portion of the main plate, and an arm of the outrigger plate may be fastened to a condylar fragment of the femur with one or more fasteners, such that the outrigger plate spans and stabilizes the Hoffa fracture.

17 Claims, 8 Drawing Sheets

(58) Field of Classification Search
USPC .................................. 606/70–71, 280–299
See application file for complete search history.

(56) References Cited

U.S. PATENT DOCUMENTS

| | | | |
|---|---|---|---|
| 6,623,486 B1* | 9/2003 | Weaver | A61B 17/8057 |
| | | | 606/281 |
| 7,090,676 B2 | 8/2006 | Huebner et al. | |
| 7,137,987 B2 | 11/2006 | Patterson et al. | |
| 7,727,264 B2 | 6/2010 | Orbay et al. | |
| 8,162,950 B2 | 4/2012 | Digeser et al. | |
| 8,382,755 B2 | 2/2013 | Austin et al. | |
| 8,394,130 B2 | 3/2013 | Orbay et al. | |
| 8,419,776 B2 | 4/2013 | Prandi et al. | |
| 8,579,898 B2 | 11/2013 | Prandi et al. | |
| 8,628,533 B2 | 1/2014 | Graham et al. | |
| 8,641,741 B2 | 2/2014 | Murashko, Jr. | |
| 8,652,179 B2 | 2/2014 | Graham et al. | |
| 8,784,419 B2 | 7/2014 | Overes et al. | |
| 8,915,918 B2 | 12/2014 | Graham et al. | |
| 8,968,371 B2 | 3/2015 | Humphrey | |
| 9,089,375 B2* | 7/2015 | Smith | A61B 17/1725 |
| | | | 606/291 |
| 9,107,704 B2 | 8/2015 | Bullard | |
| 9,956,015 B2* | 5/2018 | Ehmke | A61B 17/8009 |
| | | | 606/71 |
| 2004/0225291 A1* | 11/2004 | Schwammberger | A61B 17/80 |
| | | | 606/71 |
| 2005/0165395 A1* | 7/2005 | Orbay | A61B 17/8061 |
| | | | 606/60 |
| 2005/0234458 A1 | 10/2005 | Huebner | |
| 2005/0240187 A1 | 10/2005 | Huebner et al. | |
| 2006/0004362 A1* | 1/2006 | Patterson | A61B 17/8057 |
| | | | 606/291 |
| 2009/0275987 A1 | 11/2009 | Graham et al. | |
| 2010/0324602 A1* | 12/2010 | Huebner | A61B 17/80 |
| | | | 606/280 |
| 2013/0060251 A1 | 3/2013 | Eglseder, Jr. | |
| 2014/0163623 A1* | 6/2014 | Humphrey | A61B 17/1728 |
| | | | 606/291 |
| 2014/0172020 A1 | 6/2014 | Gonzalez-Hemandez | |
| 2015/0209092 A1 | 7/2015 | Vaidya | |
| 2015/0216574 A1 | 8/2015 | Huebner et al. | |
| 2015/0282848 A1 | 10/2015 | Vaidya | |
| 2015/0366594 A1 | 12/2015 | Berghs et al. | |
| 2016/0000481 A1 | 1/2016 | Ehmke et al. | |

FOREIGN PATENT DOCUMENTS

| | | |
|---|---|---|
| CN | 103654930 B | 11/2015 |
| DE | 102014107497 A1 | 12/2015 |

OTHER PUBLICATIONS

Thomas, Shane, Authorized Officer, International Searching Authority / US Commissioner for Patents, "Written Opinion of the International Searching Authority" in connection with related International Application No. PCT/US2017/054901, dated Dec. 5, 2017, 13 pgs.

ACUMED, "Acu-Loc 2 Extension Plates," 2017, pp. 1-5.

Extended European Search Report corresponding to Application No. 17859000.6; report dated Jun. 5, 2020; (9 pages).

* cited by examiner

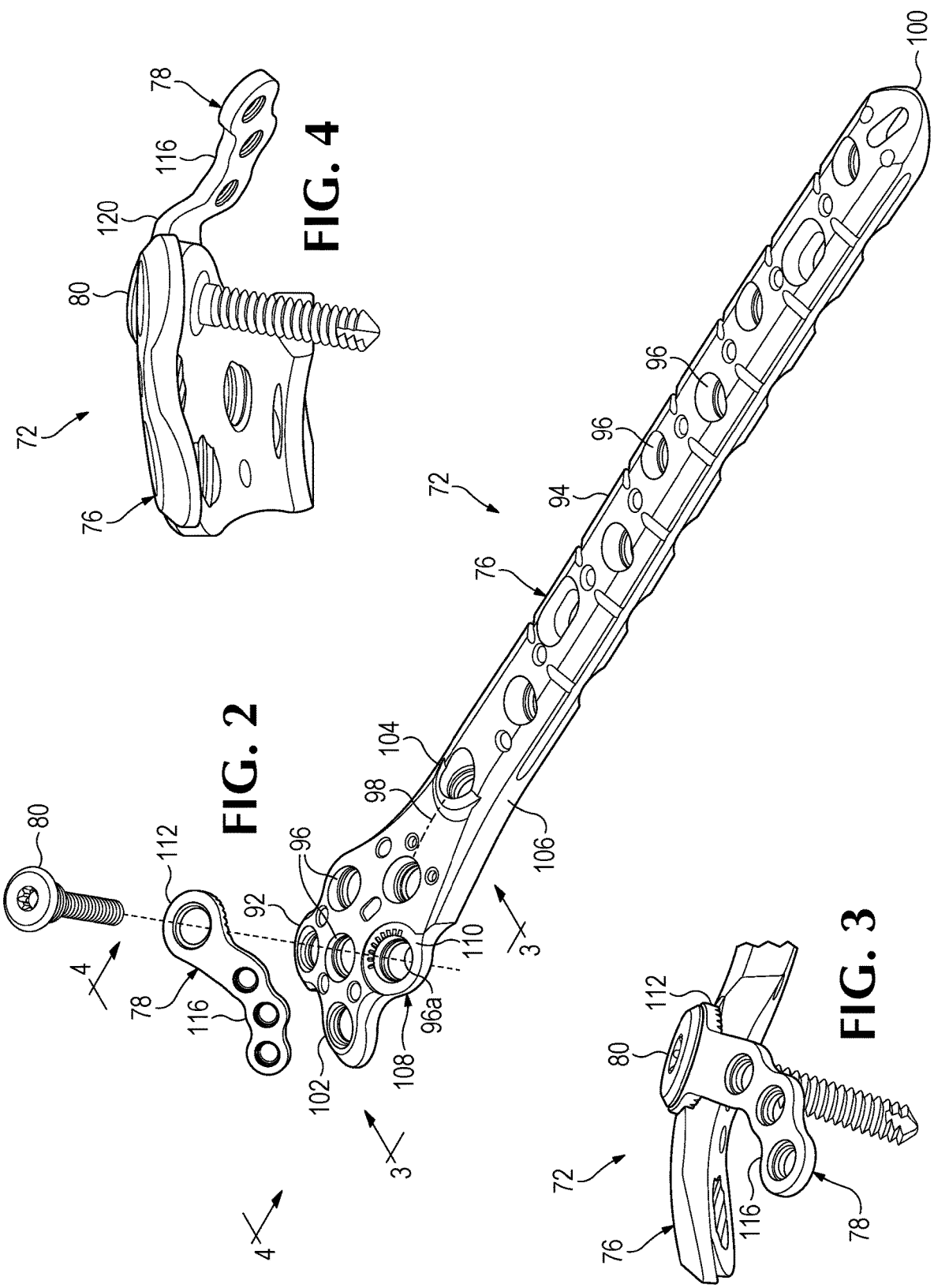

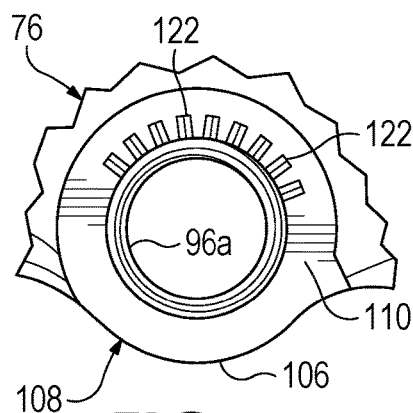
FIG. 5
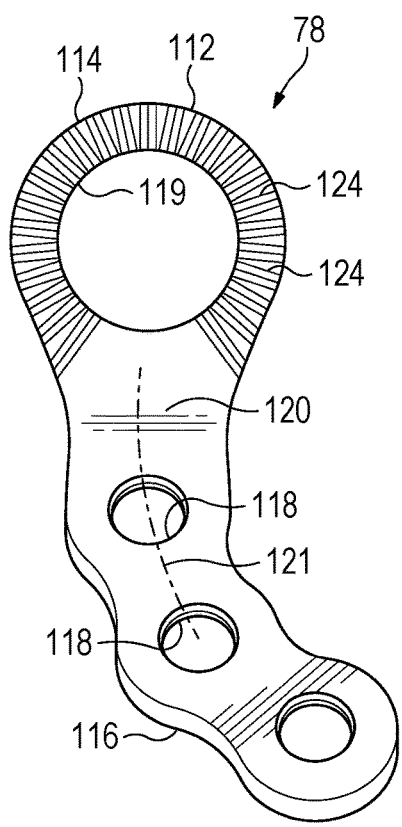
FIG. 6
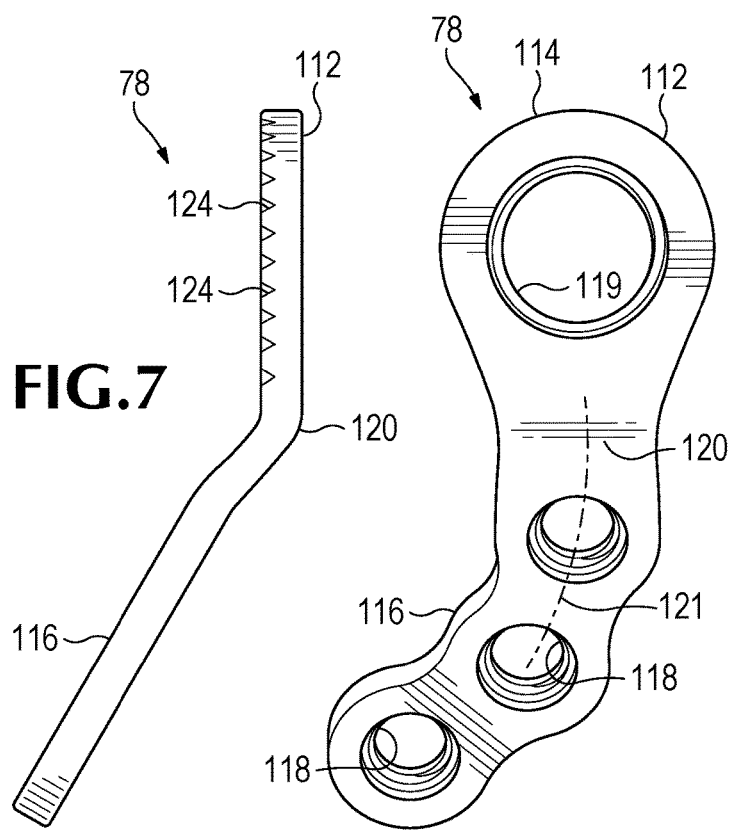
FIG. 7
FIG. 8

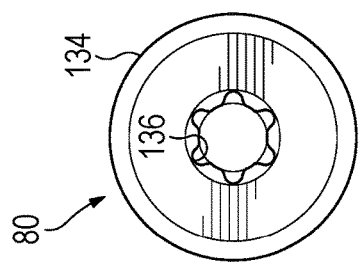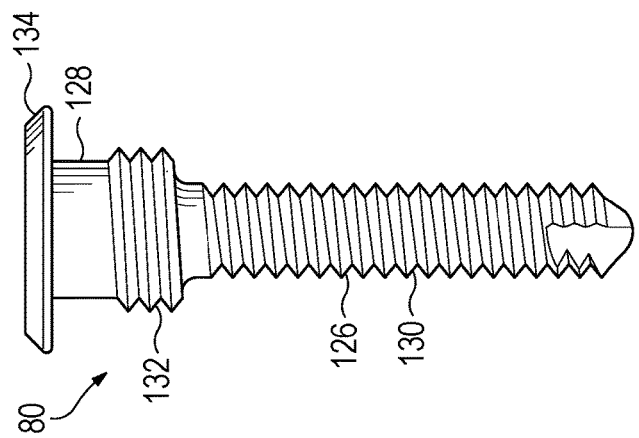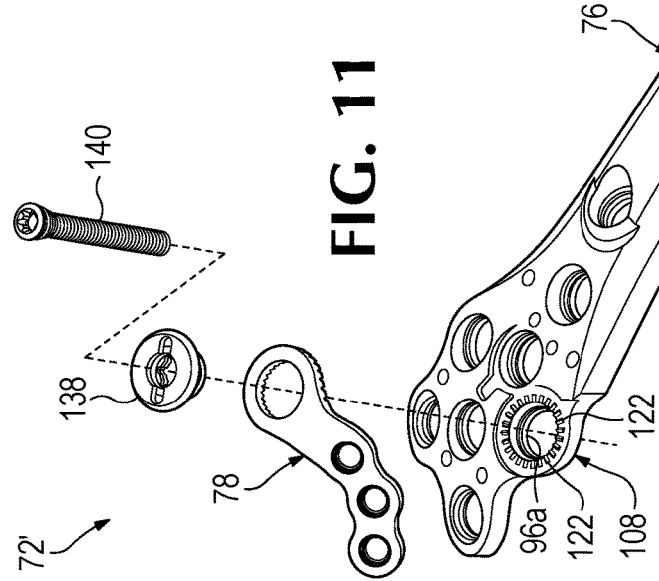

_US 10,743,923 B2_

FIXATION SYSTEM AND METHOD FOR HOFFA FRACTURES

CROSS-REFERENCE TO PRIORITY APPLICATION

This application is based upon and claims the benefit under 35 U.S.C. § 119(e) of U.S. Provisional Patent Application Ser. No. 62/404,115, filed Oct. 4, 2016, which is incorporated herein by reference in its entirety for all purposes.

INTRODUCTION

The femur articulates distally with the tibia at the knee. On the femoral side of the knee, the distal end of the femur defines a pair of rounded protuberances, known as condyles, arranged medially and laterally relative to one another. Each condyle is supported by a corresponding side of a tibial plateau created by the proximal end of the tibia.

Trauma to the femur near the knee can fracture the bone in a generally frontal plane, near or within one of the condyles, to produce a Hoffa fracture. This type of fracture generates a condylar fragment that should be stabilized to encourage osteosynthesis for restoring the integrity of the femur and function of the knee. The standard procedure for fixing a Hoffa fracture is installation of a pair of anterior-posterior (AP) bone screws, from an anterior side of the femur, across the Hoffa fracture, and into the posteriorly-located condylar fragment, to secure the condylar fragment to an anterior portion of the distal femur. However, other options for fixing a Hoffa fracture are needed, especially when the distal femur has sustained multiple fractures.

SUMMARY

The present disclosure provides a system and method for fixing a distal femur having a Hoffa fracture. The system may comprise a main plate, an outrigger plate, and a coupling member that mounts the outrigger plate to the main plate. In an exemplary method, an elongated body portion of the main plate may be secured to a shaft region of the distal femur, and a wider head portion of the main plate may be secured to an end region of the distal femur. The outrigger plate may be mounted on the head portion of the main plate, and an arm of the outrigger plate may be fastened to a condylar fragment of the femur with one or more fasteners, such that the outrigger plate spans and stabilizes the Hoffa fracture.

BRIEF DESCRIPTION OF THE DRAWINGS

FIG. 2 is an exploded, isometric view of the plate assembly of FIG. 1, taken in the absence of the femur and the tibia.

FIG. 3 is a fragmentary side view of the plate assembly of FIG. 1, taken generally along line 3-3 of FIG. 2 with plates of the plate assembly secured to one another.

FIG. 4 is a distal end view of the plate assembly of FIG. 1, taken generally along line 4-4 of FIG. 2 with plates of the assembly secured to one another.

FIG. 5 is a fragmentary, plan view of a head portion of a main plate of the plate assembly of FIG. 1, taken around an aperture of the head portion and a series of radial teeth associated with the aperture.

FIG. 6 is a bottom view of an outrigger plate of the plate assembly of FIG. 1.

FIG. 7 is a side view of the outrigger plate of FIG. 6.

FIG. 8 is a top view of the outrigger plate of FIG. 6.

FIG. 9 is a side view of a coupling member of the plate assembly of FIG. 1.

FIG. 10 is a top end view of the coupling member of FIG. 9.

FIG. 11 is an exploded isometric view of another exemplary plate assembly for the fixation system of FIG. 1.

DETAILED DESCRIPTION

The present disclosure provides a system and method for fixing a distal femur having a Hoffa fracture. The system may comprise a main plate, an outrigger plate, and a coupling member that mounts the outrigger plate to the main plate. In an exemplary method, an elongated body portion of the main plate may be secured to a shaft region of the distal femur, and a wider head portion of the main plate may be secured to an end region of the distal femur. The outrigger plate may be mounted on the head portion of the main plate, and an arm of the outrigger plate may be fastened to a condylar fragment of the femur with one or more fasteners, such that the outrigger plate spans and stabilizes the Hoffa fracture.

The fixation systems and methods disclosed herein may offer various advantages for femoral fixation, including any combination of the following. The pair of AP screws used in a standard procedure for Hoffa fixation can interfere with plate fixation of other femoral fragments, because the AP screws can block fastener trajectories determined by apertures of the plate. The systems and methods of the present disclosure can reduce the number of AP screws needed for Hoffa fixation, or eliminate the AP screws altogether, thereby permitting more plate apertures to receive fasteners and thus more effective bone fixation with the plate. Also, the systems and methods may offer a surgeon the option of expanding the footprint and fixation capability of a main (primary) bone plate on the distal femur by mounting an outrigger (secondary) plate over the main plate, if needed. The outrigger plate may be oriented selectably with respect to the main plate, according to the fracture configuration of the femur. Before or after attachment to the femur, an arm of the outrigger plate may be conformed to the local contour of the femur, and particularly a condylar fragment thereof. The size and geometry of the outrigger plate may facilitate deformation of the arm to adjust the arm's shape intraoperatively.

Further aspects of the present disclosure are described in the following sections: (I) fixation system for Hoffa fractures, (II) methods of fixing Hoffa fractures, (III) composition of system components, and (IV) examples.

I. Fixation System for Hoffa Fractures

This section describes an exemplary bone fixation system 50 to fix at least a Hoffa fracture 52 of a femur 54; see FIGS. 1-17.

Figure 1:
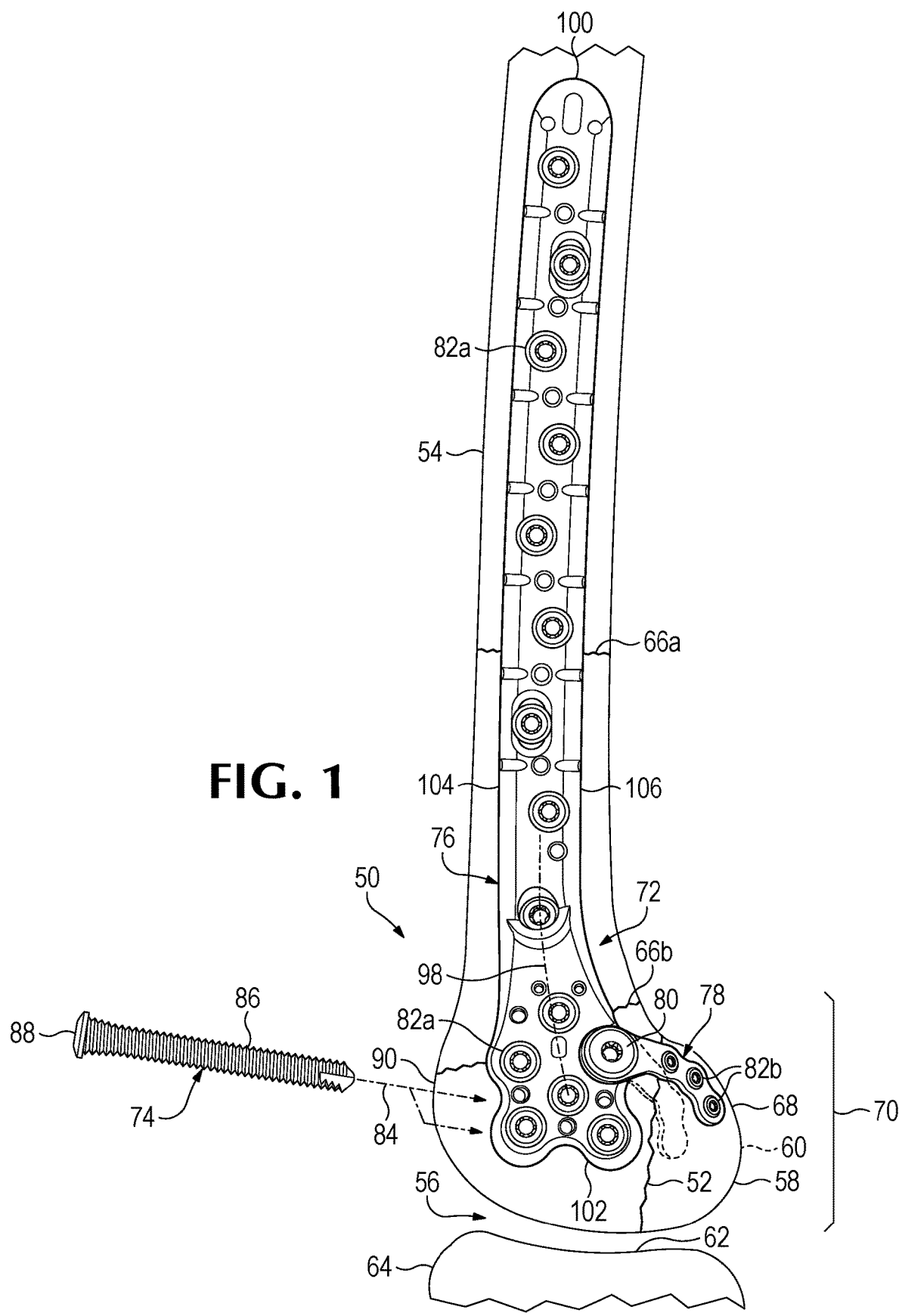
FIG. 1 is a fragmentary, lateral view of a femur and a tibia of a left leg, taken around the knee, with the femur having multiple fractures including a Hoffa fracture, with a plate assembly of an exemplary fixation system installed on the femur and spanning the Hoffa fracture, and with a Hoffa-fracture-spanning, independent, anterior-to-posterior (AP) fastener of the fixation system exploded from one of two alternative installed positions, in accordance with aspects of the present disclosure.
Figure 12:
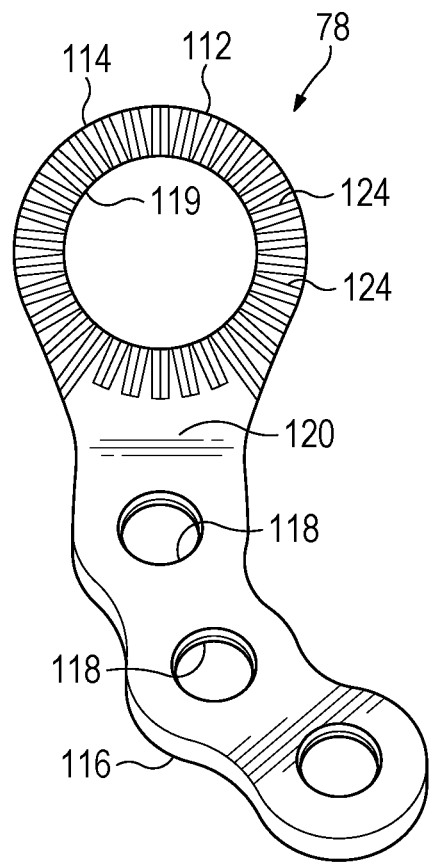
FIG. 12 is a bottom view of an outrigger plate of the plate assembly of FIG. 11.
Figure 13:
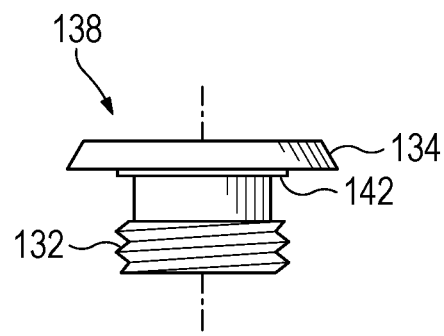
FIG. 13 is a side view of a coupling member of the plate assembly of FIG. 11.
Figure 14:
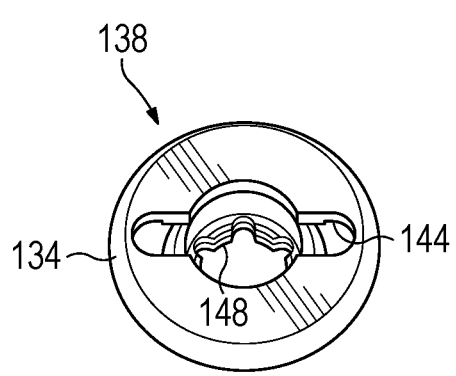
FIG. 14 is an oblique top view of the coupling member of FIG. 13.
Figure 15:
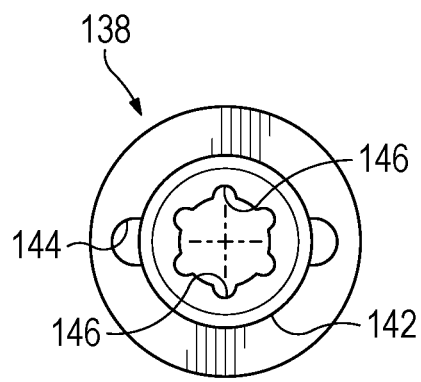
FIG. 15 is a bottom view of the coupling member of FIG. 13.

FIG. 1 shows fixation system 50 installed above a knee joint 56. The knee joint is created where lateral and medial condyles 58, 60 of the distal end of femur 54 articulate with a tibial plateau 62 formed by a proximal end of a tibia 64. In FIG. 1, anatomical axes are oriented as follows. A proximal-distal anatomical axis extends generally vertically, with proximal being above distal. An anterior-posterior anatomical axis runs generally horizontally, with anterior being leftward of posterior. A medial-lateral anatomical axis runs perpendicular to the plane of the drawing, with lateral being closer than medial.

Femur 54 may have sustained one or more fractures that are stabilized by fixation system 50, and which separate the femur into two or more pieces of bone. For example, the femur may be divided by Hoffa fracture 52 and, optionally, at least one other fracture 66*a*, 66*b*, which may (or may not) be located more proximally (i.e., farther from hip joint 56) than the Hoffa fracture. The at least one other fracture may include a fracture that is more anterior than Hoffa fracture 52, which may be a shaft (diaphyseal) fracture 66*a*, and/or a non-shaft (metaphyseal/epiphyseal) fracture 66*b* located distal to the femoral shaft and thus closer to Hoffa fracture 52.

A Hoffa fracture is any condyle-associated fracture (i.e., intracondylar and/or supracondylar) of the distal femur that is arranged at least generally in a frontal (coronal) plane, namely, within about 45 degrees of parallel to the frontal plane. The fracture creates a condylar fragment 68 including at least part of lateral condyle 58 and/or medial condyle 60, and, optionally, at least part of a respective lateral epicondyle and/or a medial epicondyle located proximally adjacent the condyle. Condylar fragment 68 may be formed from an at least predominantly posterior region of distal femur 54. The condylar fragment may represent, by volume, only a minority of an end portion 70 of the distal femur, where the end portion is the entire fraction of the femur located distal to the femoral shaft.

The fixation system may include a plate assembly 72 and at least one AP (anterior-to-posterior) fastener 74 (also called an independent fastener) that separately and respectively span Hoffa fracture 52 outside and inside femur 54. The plate assembly may have a main plate 76 (also called a primary plate), an outrigger plate 78 (also called an ancillary or secondary plate), and a coupling member 80 that firmly attaches plates 76, 78 to one another, optionally independent of bone and/or at a selectable orientation. Each of main plate 76 and outrigger plate 78 may be secured to femur 54 with respective sets of fasteners 82*a*, 82*b*, which may be threaded fasteners, such as bone screws. The outrigger plate optionally may be secured to condylar fragment 68 with fasteners that are smaller (narrower/shorter) than the fasteners for the main plate. In the depicted embodiment, each of fasteners 82*b* extending through apertures of outrigger plate 78 are smaller in diameter and shorter than each of fasteners 82*a* extending through apertures of main plate 76. Each fastener of the fixation system (e.g., fasteners 74, 82*a*, and 82*b*) independently may, for example, be a screw, peg, pin, staple, cable, wire, rivet, or the like.

AP fastener 74 is shown in FIG. 1 exploded from two alternative installed configurations, indicated by a branched arrow at 84 extending approximately along an anterior-posterior anatomical axis defined by the femur. The AP fastener may be oriented relatively more perpendicular to Hoffa fracture 52, and at least a majority of fasteners 82*b* may be oriented relatively more parallel to the fracture. The AP fastener(s) may provide primary fixation of the Hoffa fracture, and plate assembly 72 may provide supplemental fixation thereof. Each AP fastener may, for example, be a bone screw having an external thread 86 to engage bone, and a head 88 at which the bone screw engages a driver for advancing the screw into bone. The head may be disposed at an anterior side 90 of the femur, and the bone screw may extend posteriorly in the bone from the anterior side. The external thread may be configured to engage femur 54 on both sides of Hoffa fracture 52, or the bone screw may be a lag screw with a thread that engages only condylar fragment 68, among others. AP fastener 74 may stabilize bone independently of plate assembly 72. For example, the AP fastener may provide no attachment of plate assembly 72 to bone, and may not enter any aperture of the plate assembly when installed.

Outrigger plate 78 may be firmly attached to main plate 76 by coupling member 80 at a fixed orientation, which may be selected from a plurality of different permitted orientations. One alternative orientation for the outrigger plate is shown in phantom outline in FIG. 1. The outrigger plate may be adjusted to any of the permitted orientations by rotating the outrigger plate relative to the main plate in a plane about an orthogonal axis extending through and defined by a pair of coaxially aligned apertures of the plates, before coupling member 80 is tightened to fix the orientation. The outrigger plate may be configured to be adjustable discretely in the plane by one or more predefined angular increments, or may be adjustable and then fixed over a continuous range of orientations in the plane. If adjustable discretely, the orientations may be uniformly offset from one another. A suitable predefined angular increment of adjustment for the plate assembly may, for example, be less than 30, 20, or 15 degrees, among others, and/or greater than 2, 3, or 4 degrees, among others.

FIGS. 2-4 show plate assembly 72 in exploded and assembled configurations. Main plate 76 forms a platform onto which outrigger plate 78, if needed, may be mounted by coupling member 80. The main plate may be substantially larger and sturdier than the outrigger plate, to provide primary fixation of the femur (for one or more fractures other than the Hoffa fracture). For example, each of the length and/or the average width of the main plate, independently may be at least about 1.5, 2, 3, 4, or 5 times the length and/or average width of the outrigger plate. Also or alternatively, the average thickness of the main plate may be at least about 20%, 40%, 60%, 80%, or 100% greater than the average thickness of the outrigger plate. Accordingly, the outrigger plate may be much more amenable than the main plate to deformation intra-operatively, for adjusting the shape of the outrigger plate, but may be configured to bear a much smaller load than the main plate.

Main plate 76 may have any suitable structure. For example, the main plate may have a distal head portion 92 extending from a proximal body portion 94, and optionally formed integrally with one another (see FIG. 2). Head portion 92 may be wider, on average, than body portion 94. The head portion may be contoured to fit onto a surface region of end portion 70 of the femur (also see FIG. 1), and thus may have an inner, bone facing surface that is complementary to the surface region. Body portion 94 may be elongated and, in some cases, substantially linear. The body portion may be substantially longer than the head portion of the main plate, such as at least 2, 3, 4, or 5 times as long. The inner, bone facing surface of the body portion may be concave transversely to provide a better fit of the body portion onto the femoral shaft. Each of head portion 92 and body portion 94 may define a plurality of apertures 96, any of which may be internally threaded, to provide locking attachment to corresponding, externally-threaded fasteners that extend into the femur. Each of apertures 96 may be circular, or may be elongated orthogonal to a through-axis of the aperture.

Main plate 76 defines a centerline 98 that extends between opposite ends of the plate (i.e., between a proximal end 100 formed by body portion 94 and a distal end 102 formed by head portion 92). The centerline is generally centered between opposite longitudinal edges of the plate, namely, an anterior edge 104 and a posterior edge 106. Centerline 98 may be curved, as in the depicted embodiment, or linear.

Head portion 92 (and/or body portion 94) also may define an attachment site 108 at which outrigger plate 78 is configured to overlap with, and be attached to, main plate 76 (see FIGS. 2 and 5). The attachment site may include at least one of apertures 96, labeled as 96a, which may be the same diameter as other apertures 96 of the main plate, offering a surgeon the option of inserting identical threaded fasteners into bone from the attachment site and other apertures of the main plate, if the surgeon chooses not to use the outrigger plate. Each of apertures 96, including aperture 96a, may have an internal thread that is complementary to an external thread of the same threaded fastener.

Aperture 96a may have any suitable position within head portion 92 of main plate 76. The aperture may be offset from centerline 98. For example, the through-axis and/or all of aperture 96a may be spaced posteriorly from centerline 98, and/or aperture 96a may be located closer to posterior edge 106 than anterior edge 104. In some embodiments, the main plate may be conceptually divided in a pair of lateral portions each bounded in part by the centerline and a different one of the longitudinal edges of the main plate, and the outrigger plate may overlap only one of the lateral portions when mounted to the main plate. Head portion 92 of the main plate may have at least one other aperture 96 that is spaced distally or proximally from aperture 96a, and/or at least one other aperture 96 that is spaced anteriorly from aperture 96a. Accordingly, the position of aperture 96a may be described as proximal (or distal) and/or posterior within the head portion of the main plate. Attachment site 108 and/or aperture 96a may be defined at least in part by protrusion of the head portion that protrudes laterally with respect to centerline 98.

The thickness of head portion 92 may decrease at attachment site 108, to reduce the combined thickness of main plate 76 and outrigger plate 78 where they overlap. For example, head portion 92 may define a recess 110 (e.g., a planar recess) in the outer surface of attachment site 108 that is configured to receive part of the outrigger plate (see FIG. 5).

Outrigger plate 78 may have any suitable structure (see FIGS. 2-4 and 6-8). For example, the outrigger plate may have a mounting region or head 112 configured to overlap main plate 76 at attachment site 108, with the mounting region disposed over an outer surface of the main plate that faces away from the femur. The mounting region may form a loop 114 through which coupling member 80 extends. The outrigger plate also may have a non-overlapping arm or tail 116, which may project transversely away from the main plate at posterior edge 106 thereof. Arm 116 may have a smaller average width than mounting region 112. The arm may be elongated (linearly or non-linearly), and may define one or more apertures 118, which may (or may not) be internally threaded, to provide locking attachment to corresponding, externally-threaded fasteners 82b that extend into the femur (also see FIG. 1). Apertures 118 of arm 116 of the outrigger plate may (or may not) be smaller in diameter than apertures 96 of the main plate and/or of an aperture 119 of loop 114, such as less than about 80%, 70%, or 60% of the diameter of apertures 96 and/or aperture 119.

The outrigger plate may have a junction region 120 between mounting region 112 and arm 116 that creates an offset in elevation between these parts of the outrigger plate (see FIGS. 4 and 7). More particularly, the junction region may bend inward and then slightly outward at positions respectively adjacent and spaced from mounting region 112. With this configuration, once the outrigger plate is mounted on the main plate, the inner (bone-facing) surface of arm 116 may be approximately flush with the inner surface of head portion 92, such that both surfaces can contact the femur.

Outrigger plate 78 may be curved longitudinally, in the plane of the plate, to avoid a site of muscle attachment on the femur. For example, the outrigger plate may have a curved centerline 121 when projected orthogonally onto a plane parallel to mounting region 112 (see FIGS. 6 and 8).

The main plate also may define a lower interface region of an interface at which main plate 76 and outrigger plate 78 grip one another (see FIGS. 2 and 5-7). The lower interface region may be configured to mesh with a complementary, upper interface region defined by mounting region 112, at only a finite series of orientations of plate 78. The interface restricts rotation of the main plate and outrigger plate relative to one another about a central through-axis of the attachment site, after the regions of the interface are tightened against one another with coupling member 80. In the depicted embodiment, the lower interface region has a plurality of radially-arranged protrusions 122 (see FIG. 5) that mesh with corresponding radial indentations 124 defined by the inner surface of mounting region 112 (see FIGS. 6 and 7). The angular offset of the protrusions (and/or the angular offset of the indentations) from one another determines the increment of angular adjustment permitted by the interface. For example, in the depicted embodiment, the protrusions and indentations provide a 12-degree increment of adjustment at the interface, although any suitable increment of adjustment may be provided. The protrusions and indentations may be formed along any suitable portion of the circumference of respective apertures 96a and 119. For example, the protrusions may be formed along less than one-half of the circumference of aperture 96a, to simplify manufacturing and reduce the change of breakage of the main plate at attachment site 108. In other embodiments, the complementary surface features of the interface may be omitted, such that the interface relies primarily on friction to resist rotational slippage of the main plate and the outrigger plate relative to one another. In these embodiments, one or both of the surfaces of the interface that face and contact one another may be roughened (e.g., grit blasted) to create a texture that resists slippage.

Outrigger plate may be firmly mounted to the main plate over a range of orientations. The range may be at least about 25, 30, 35, 40, 45, or 50 degrees, among others. The outrigger plate may overlap none of the other screw-receiving apertures 96 of the head portion, besides aperture 96a, over the range of orientations, thus avoiding obstruction that would prevent placement of screws into these apertures.

FIGS. 9 and 10 show coupling member 80 in more detail. The coupling member, which may be described as a set screw, may have an elongated shaft 126 and an enlarged head 128 located at the trailing end of shaft 126. The shaft may have an external thread 130 to engage bone. The coupling member also may have another external thread 132 formed distally on head 128 for threaded engagement with a complementary internal thread of aperture 96a (also see FIG. 2). Head 128 may be nonthreaded proximally where the head will be encircled by loop 114 (also see FIG. 8). The head further may have a flange 134 at a trailing end thereof. When the coupling member is tightened against the outrigger plate, mounting region 112 of the outrigger plate may be clamped between flange 134 of coupling member 80 and attachment site 108 of main plate 76, to fix the orientation of the outrigger plate. A driver-engagement structure 136 may be defined internally and/or externally by head 128, to allow a driver to rotationally advance the coupling member into operative engagement with plates 76, 78.

FIGS. 11-15 show another plate assembly 72' for bone fixation system 50. Plate assembly 72' is similar in structure and function to its unprimed relative (see FIG. 2), but differs as follows. First, main plate 76 has an attachment site 108 with protrusions 122 fully encircling the through-axis of aperture 96a. Second, outrigger plate 78 defines indentations 124 that fully encircle aperture 119 of loop 114 (see FIG. 12). The presence of more protrusions and indentations than in plate assembly 72 provides more extensive meshing and better purchase at the interface between the plates, while making both plates slightly less sturdy. Third, coupling member 80 of plate assembly 72 is replaced by two separate components, namely, a coupling member 138 and an optional bone screw 140. In some embodiments, bone screw 140 may be identical to fastener 82b.

Coupling member 138 is effectively a truncated version of coupling member 80 that is missing shaft 126 (compare with FIG. 9), such that coupling member 138 does not extend substantially into bone. The truncated coupling member has external thread 132 for engagement with aperture 96a of the main plate, a nonthreaded region that is encircled by loop 114 of the outrigger plate, and flange 134 (see FIG. 13). However, a seating protrusion 142 may be formed on the underside of the flange (and may be included in coupling member 80). The protrusion may be sized to be received in loop 114 of the outrigger plate. The protrusion may function to center aperture 119 of the loop on the central axis of the coupling member as the coupling member is tightened, and, optionally, to engage an edge of aperture 119, to prevent transverse motion of the outrigger plate.

Coupling member 138 may define any suitable structure for operative engagement with a driver, to allow the coupling member to be turned with the driver. For example, the coupling member may define a transverse slot 144 and a circumferentially distributed arrangement of cutouts 146, which may be complementary to a suitable driver(s) (see FIGS. 14 and 15). Each cutout 146 may be formed in an internal thread 148 defined by the coupling member. The internal thread may be utilized to lock bone screw 140 to the coupling member after the coupling member has been tightened and the driver removed (also see FIG. 11), or coupling member 138 may be assembled with bone screw 140 first, and then the assembly installed as a unit. Bone screw 140 can extend into bone, to secure the main plate and/or the outrigger plate to a region of bone located directly under attachment site 108 of main plate 76.

Figure 16:
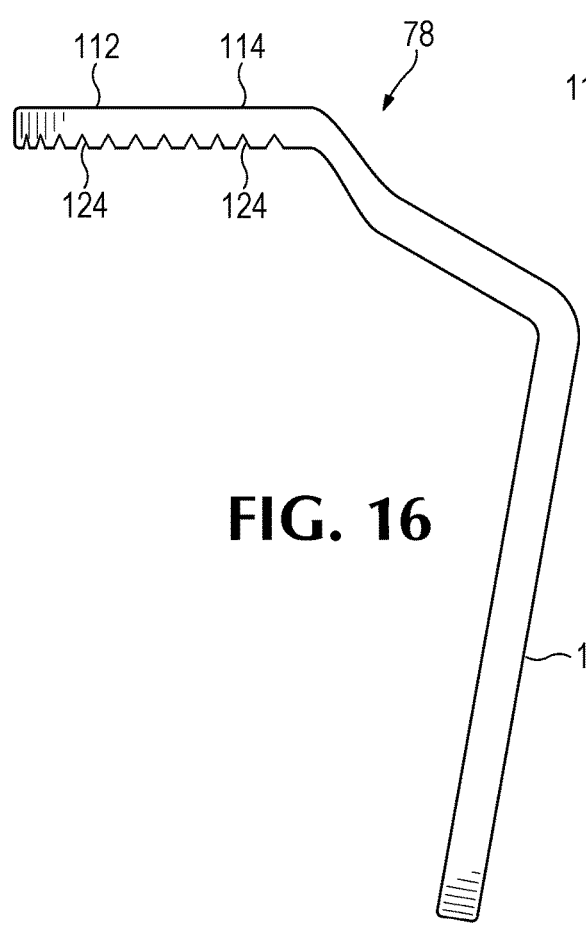
FIG. 16 is a side view of a longer, more bent embodiment of an outrigger plate for the plate assemblies of FIGS. 1 and 11.
Figure 17:
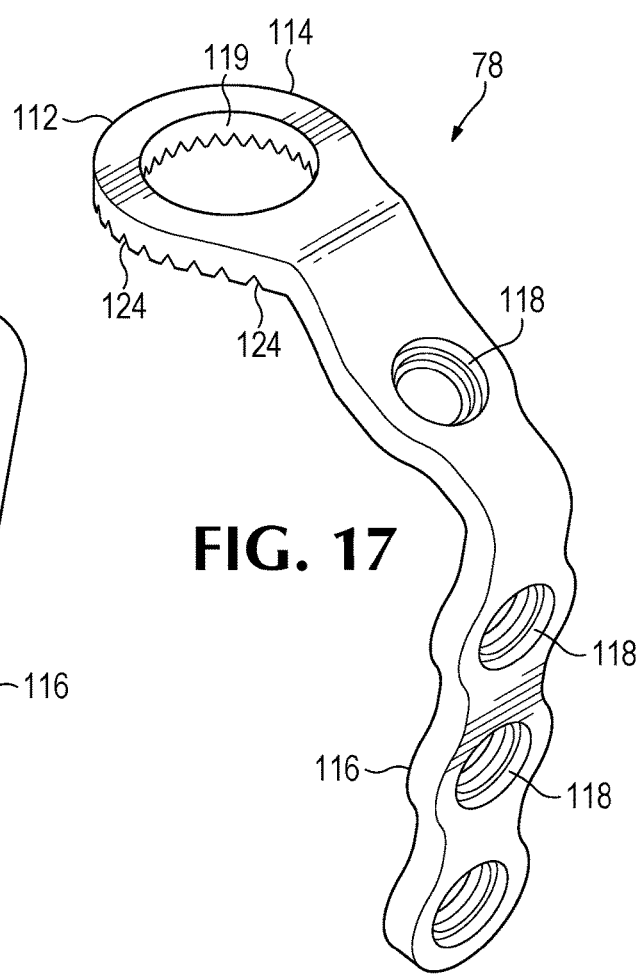
FIG. 17 is another view of the outrigger plate of FIG. 16.
Figure 18:
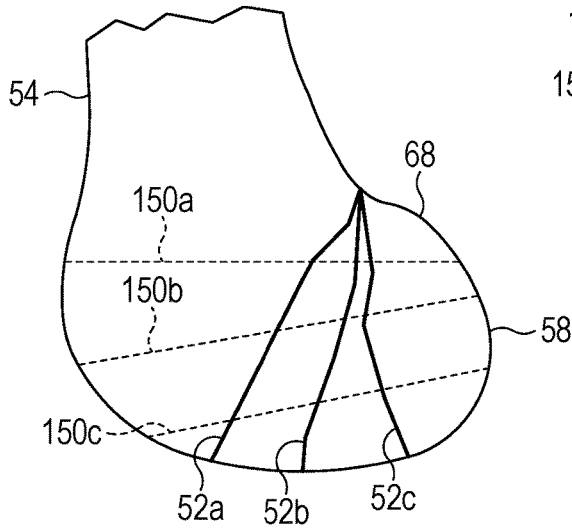
FIGS. 18-21 are respective lateral, posterolateral, anterior, and posterior views of the distal region of a femur, with exemplary Hoffa fracture patterns and AP fastener trajectories marked, in accordance with aspects of the present disclosure.
Figure 19:
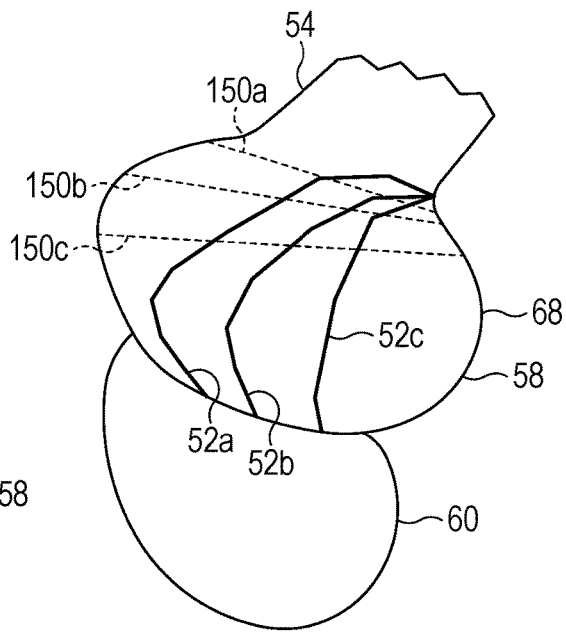

FIGS. 16 and 17 show a longer version of outrigger plate 78 for plate assembly 72 or 72'.

II. Methods of Fixing Hoffa Fractures

This section describes exemplary methods of fixing a femur having at least a Hoffa fracture, with the systems of the present disclosure. The method steps of this section and/or disclosed elsewhere herein, may be performed in any suitable order and combination, using any combination of the devices (and/or device features) of the present disclosure.

A fractured bone may be selected for fixation. The bone may be a femur 54 that has been fractured to create a Hoffa fracture 52 and, optionally, at least one other fracture in a distal region of the femur. The Hoffa fracture may create any suitable number of condylar bone fragments 68, such as 1, 2, 3, 4, 5, or more. In other embodiments, the bone may be a humerus having a distal fracture, optionally including a humeral condyle.

At least one AP fastener 74 may be placed into femur 54. Placement of one or more fasteners 74 may be performed before, after, or both before and after installation of plates 76 and 78. Each fastener 74 may be placed into a pre-drilled hole in the femur, or may be self-drilling to form its own hole. The path followed by each fastener 74 into the femur may be defined by a pre-installed K-wire. For example, the hole for fastener 74 may be drilled around the K-wire, with the K-wire guiding axial travel of a drill. Before drilling and fastener 74 insertion, the path of the K-wire may be visualized with fluoroscopy, to check whether the path will result in proper fastener placement. The fastener may be inserted in an anterior to posterior direction, such that the fastener extends across the Hoffa fracture.

Main plate 76 may be secured to femur 54 with a plurality of plate fasteners 82a, such as bone screws. Full insertion of plate fasteners 82a into one or more apertures of the main plate may be obstructed by one or more AP fasteners. Accordingly, one or more apertures of head portion 92 may be left unoccupied. In some embodiments, the main plate may be positioned on the femur and secured, with outrigger plate 78 pre-mounted on the main plate.

Outrigger plate 78 may be firmly attached to main plate 76 with a coupling member at a selected orientation. The outrigger plate also may be secured to condylar fragment 68 with one or more plate fasteners 82b. At least one fastener 82b may be placed into bone from the coupling member, and may be locked to the coupling member by threaded engagement.

III. Composition of System Components

The plates, coupling member, and fasteners of the present disclosure may have any suitable composition. Each may be formed of any suitable biocompatible material(s) and/or bioresorbable (bioabsorbable) material(s). Illustrative biocompatible materials that may be suitable include (1) metal (for example, titanium or titanium alloy, cobalt-chrome alloy, stainless steel, etc.); (2) polymer/plastic (for example, ultra-high molecular weight polyethylene (UHMWPE), polymethylmethacrylate (PMMA), polytetrafluoroethylene (PTFE), polyetheretherketone (PEEK), and/or PMMA/polyhydroxyethylmethacrylate (PHEMA)); (3) bioresorbable material or polymer/plastic (for example, polymers of α-hydroxy carboxylic acids (e.g., polylactic acid (such as PLLA, PDLLA, and/or PDLA), polyglycolic acid, lactide/glycolide copolymers, etc.), polydioxanones, polycaprolactones, polytrim ethylene carbonate, polyethylene oxide, poly-β-hydroxybutyrate, poly-β-hydroxypropionate, poly-δ-valerolactone, poly(hydroxyalkanoate)s of the PHB-PHV class, other bioresorbable polyesters, and/or natural polymers (such as collagen or other polypeptides, polysaccharides (e.g., starch, cellulose, and/or chitosan), any copolymers thereof, etc.)); (4) bone material or bone-like material (e.g., bone chips, calcium phosphate crystals (e.g., hydroxyapatite, carbonated apatite, etc.)); or (5) any combination thereof.

The main plate and the outrigger plate may be formed of the same or different materials. For example, each may be formed of metal, of the same or different composition.

IV. EXAMPLES

The following examples describe further exemplary aspects of the fixation systems and methods of the present disclosure. These examples are intended for illustration only, and should not limit the entire scope of the present disclosure.

Example 1

Exemplary Hoffa Fractures and AP Fastener Trajectories

Figure 20:
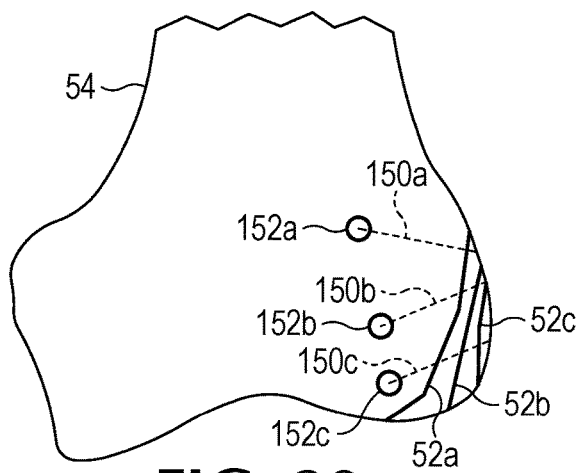
Figure 21:
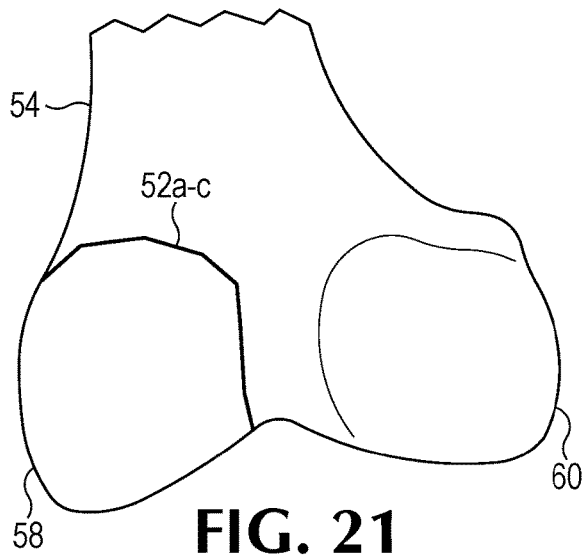

This example describes further aspects of Hoffa fractures and suitable AP fastener trajectories therefor. FIGS. 18-21 show respective lateral, posterolateral, anterior, and posterior views of the distal region of a femur, with exemplary Hoffa fracture patterns 52a-c and AP fastener trajectories 150a-c marked. Respective femoral entry sites 152a-c for trajectories 150a-c are shown in FIG. 20.

Example 2

Testing Fixation Configurations with a Model Femur

Figure 22:
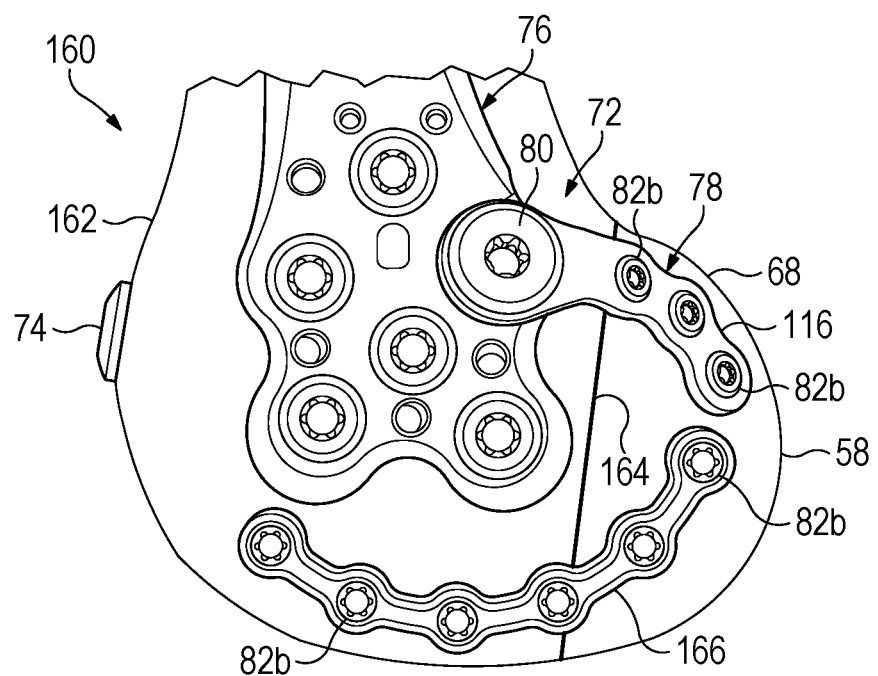
FIG. 22 is a fragmentary view of one of a series of different fixation configurations that were tested for stabilization of a model femur having a Hoffa-like cut, in accordance with aspects of the present disclosure

This example describes exemplary test results obtained with a test system 160; see FIG. 22.

System 160 includes a model femur 162 having a Hoffalike cut 164 that creates a condylar fragment 68. Fixation devices were attached to model femur 162 in various configurations, and then an increasing axial load was applied to the condylar fragment while monitoring the condylar fragment for displacement. This analysis permitted determination of the stiffness and maximum load for each fixation configuration. FIG. 22 illustrates a fixation configuration generated with a working model of plate assembly 72 (see FIG. 1), a single AP fastener 74, and a rim plate 166 spanning Hoffa-like cut 164. The rim plate may be curved, as depicted, or linear, in plan view.

Fixation configurations that were tested are listed in the following table:

TABLE 1

Tested fixation configurations

| Designation | Fixation Configuration |
| --- | --- |
| A | Two AP fasteners 74 |
| B | Two AP fasteners 74 + main plate 76 |
| C | One AP fastener 74 + main plate 76 |
| D | One AP fastener 74 + plate assembly 72 |
| E | One AP fastener 74 + plate assembly 72 + rim plate 166 |
| F | Plate assembly 72 + rim plate 166 |

The relative strength and stiffness of the configurations were found to be C<A/B<D<E/F, where A is similar to B, and E to F. Accordingly, the use of plate assembly 72 may allow only one AP bone screw to be installed, and the use of plate assembly 72 plus rim plate 166 may allow a surgeon to omit installation of AP bone screws 74 altogether.

Example 3

Selected Embodiments A

This example describes selected embodiments of exemplary methods of fixing a fractured distal femur having a Hoffa fracture. The selected embodiments are presented as a series of numbered paragraphs.

Paragraph 1. A method of fixing a fractured distal femur having a fracture creating a condylar fragment including at least a portion of the lateral condyle or medial of the distal femur, the method comprising, in any order: (A) securing a main plate having an elongated body portion and a head portion to a fractured distal femur, wherein the elongated body portion is secured to a shaft region of the distal femur, and wherein the head portion is secured to an end region of the distal femur; (B) mounting an outrigger plate to the head portion of the main plate at a selectable orientation with respect to the main plate; and (C) fastening the outrigger plate to the condylar fragment with one or more fasteners.

Paragraph 2. The method of paragraph 1, wherein the step of mounting an outrigger plate includes a step of mounting an outrigger plate that is substantially shorter, narrower, and thinner than the main plate.

Paragraph 3. The method of paragraph 1, wherein the step of mounting an outrigger plate includes a step of selecting an orientation of the outrigger plate from a series of discrete orientations permitted by an interface formed collectively by the main plate and the outrigger plate.

Paragraph 4. The method of paragraph 3, wherein the step of mounting an outrigger plate includes a step of clamping an loop of the outrigger plate between the main plate and a coupling member.

Paragraph 5. The method of paragraph 1, wherein the step of securing a main plate is performed with larger bone screws, and wherein the step of fastening the outrigger plate is performed with smaller bone screws.

Paragraph 6. The method of paragraph 1, further comprising a step of placing an independent fastener into the distal femur from an anterior side thereof, such that the independent fastener spans the Hoffa fracture and does not enter any aperture of the main plate and does not enter any aperture of the outrigger plate.

Paragraph 7. The method of paragraph 6, wherein the independent fastener is threaded externally.

Paragraph 8. The method of paragraph 6, wherein the independent fastener has a first orientation with respect to the Hoffa fracture, wherein the one or more fasteners that fasten the outrigger plate to the condylar fragment have a second orientation or average second orientation with respect to the Hoffa fracture, and wherein the first orientation is more perpendicular to the Hoffa fracture than the second orientation or average second orientation.

Example 4. Selected Embodiments B

This example describes additional selected embodiments of exemplary methods of fixing a fractured distal femur having a Hoffa fracture. The selected embodiments are presented as a series of numbered paragraphs.

Paragraph 1. A method of fixing a distal femur having a Hoffa fracture creating a condylar fragment, the method comprising, in any order: (A) securing a main plate having an elongated body portion and a head portion to the distal femur, wherein the elongated body portion is secured to a shaft region of the distal femur, and wherein the head portion is wider than the body portion and is secured to an end region of the distal femur; (B) selecting an orientation for an outrigger plate from two or more orientations permitted by an interface between the main plate and the outrigger plate; (C) mounting the outrigger plate firmly on the head portion of the main plate at the selected orientation with a coupling member; and (D) fastening an arm of the outrigger plate to the condylar fragment with one or more fasteners such that the outrigger plate spans and stabilizes the Hoffa fracture.

Paragraph 2. The method of paragraph 1, wherein the outrigger plate is substantially shorter, narrower, and thinner than the main plate.

Paragraph 3. The method of paragraph 1 or paragraph 2, wherein the step of selecting an orientation for an outrigger plate includes a step of selecting an orientation from a finite series of discrete orientations permitted by the interface between the main plate and the outrigger plate.

Paragraph 4. The method of paragraph 3, wherein the step of mounting an outrigger plate includes a step of clamping a loop of the outrigger plate between the head portion of the main plate and a flange of the coupling member.

Paragraph 5. The method of any one of paragraphs 1 to 4, wherein the step of securing a main plate is performed with larger bone screws, and wherein the step of fastening an arm of the outrigger plate is performed with smaller bone screws.

Paragraph 6. The method of any one of paragraphs 1 to 5, further comprising a step of attaching a fixation device to the distal femur such that the fixation device spans the Hoffa fracture independently of the main plate and the outrigger plate and does not enter any aperture of the main plate and does not enter any aperture of the outrigger plate.

Paragraph 7. The method of paragraph 6, wherein the step of attaching a fixation device includes a step of placing a threaded fastener into the distal femur from an anterior side thereof and across the Hoffa fracture.

Paragraph 8. The method of paragraph 6 or paragraph 7, wherein the main plate and the outrigger plate are a first plate and a second plate, and wherein the step of attaching a fixation device includes a step of attaching a third plate to the distal femur such that the third plate spans and stabilizes the Hoffa fracture.

Paragraph 9. The method of any one of paragraphs 1 to 8, wherein the coupling member has an external thread that is complementary to an internal thread formed in each of a plurality of apertures defined by the head portion.

Paragraph 10. The method of any one of paragraphs 1 to 9, wherein the head portion of the main plate defines a plurality of apertures configured to receive bone screws, wherein the plurality of apertures have the same diameter as one another, wherein the step of mounting the outrigger plate includes a step of mounting an aperture of the outrigger plate coaxial to a first aperture of the plurality of apertures, and wherein the first aperture is spaced proximally or distally on the distal femur from at least one aperture of the plurality of apertures and is spaced posteriorly on the distal femur from at least one aperture of the plurality of apertures.

Paragraph 11. The method of any one of paragraphs 1 to 10, wherein the outrigger plate has a mounting region that overlaps the main plate, wherein the mounting region is wider than the arm, and wherein the outrigger plate has a curved centerline when projected orthogonally onto a plane parallel to the mounting region.

Paragraph 12. The method of any one of paragraphs 1 to 11, wherein the main plate defines a longitudinal center line that conceptually divides the main plate into a pair of lateral portions each bounded in part by the center line and a longitudinal edge of the main plate, and wherein the outrigger plate overlaps only one of the lateral portions after the step of mounting the outrigger plate.

Paragraph 13. A method of fixing a distal femur having a Hoffa fracture creating a condylar fragment, the method comprising, in any order: (A) securing a main plate having an elongated body portion and a head portion to the distal femur, wherein the elongated body portion is secured to a shaft region of the distal femur, and wherein the head portion is wider than the body portion and is secured to an end region of the distal femur; (B) clamping a mounting region of an outrigger plate between the head portion of the main plate and a flange of a coupling member at a rotational position selected from two or more permitted rotational positions of the mounting region, wherein the outrigger plate is shorter, narrower, and thinner than the main plate; and (C) fastening an arm of the outrigger plate to the condylar fragment with one or more fasteners such that the outrigger plate spans and stabilizes the Hoffa fracture, wherein the arm is narrower than the mounting region.

Paragraph 14. The method of paragraph 13, further comprising a step of attaching a fixation device to the distal femur such that the fixation device spans the Hoffa fracture independently of the main plate and the outrigger plate and does not enter any aperture of the main plate and does not enter any aperture of the outrigger plate.

Paragraph 15. The method of paragraph 14, wherein the step of attaching a fixation device includes a step of placing a threaded fastener into the distal femur from an anterior side thereof.

Paragraph 16. The method of paragraph 14 or paragraph 15, wherein the main plate and the outrigger plate are a first plate and a second plate, and wherein the step of attaching a fixation device includes a step of attaching a third plate to the distal femur such that the third plate spans and stabilizes the Hoffa fracture.

Paragraph 17. The method of any one of paragraphs 13 to 16, wherein the coupling member is a set screw having an external thread that is complementary to an internal thread formed in each of a plurality of apertures defined by the head portion.

Paragraph 18. The method of any one of paragraphs 13 to 17, wherein the head portion of the main plate defines a plurality of apertures configured to receive bone screws, wherein the step of clamping includes a step of mounting an aperture of the outrigger plate coaxial to a first aperture of the plurality of apertures, and wherein the first aperture is spaced proximally or distally on the distal femur from at least one aperture of the plurality of apertures and posteriorly on the distal femur from at least one other aperture of the plurality of apertures.

Paragraph 19. The method of paragraph 18, wherein each aperture of the plurality of apertures has an internal thread of the same diameter.

Paragraph 20. A method of fixing a distal femur having a Hoffa fracture creating a condylar fragment, the method comprising, in any order: (A) securing a main plate having an elongated body portion and a head portion to the distal femur using a plurality of larger bone screws, wherein the elongated body portion is secured to a shaft region of the distal femur, wherein the head portion is wider than the body portion and is secured to an end region of the distal femur, wherein the main plate has a proximal end, a distal end, and a pair of longitudinal edges opposite one another on the main plate and each extending from the proximal end to the distal end of the main plate, and wherein the main plate defines a longitudinal center line that conceptually divides the main plate into a pair of lateral portions each bounded in part by the center line and a different one of the longitudinal edges; (B) mounting a loop of an outrigger plate firmly between the head portion of the main plate and a flange of a coupling member at a rotational position selected from a plurality of permitted rotational positions of the loop, such that the outrigger plate extends past one of the longitudinal edges of the main plate, wherein the outrigger plate has a curved centerline when projected orthogonally onto a plane parallel to the loop and is shorter, narrower, and thinner than the main plate, wherein the outrigger plate overlaps only one of the lateral portions of the main plate when mounted to the main plate, wherein the head portion of the main plate defines a plurality of apertures configured to receive bone screws, and wherein the step of mounting includes a step of mounting an aperture of the loop coaxial to a first aperture of a plurality of apertures defined by the head portion of the main plate, and wherein the first aperture is spaced proximally or distally on the distal femur from at least one aperture of the plurality of apertures and posteriorly on the distal femur from at least one other aperture of the plurality of apertures; and (C) fastening an arm of the outrigger plate to the condylar fragment with one or more smaller bone screws such that the outrigger plate spans and stabilizes the Hoffa fracture.

Paragraph 21. A system for fixing a distal femur having a Hoffa fracture creating a condylar fragment, the system comprising: (A) a main plate having an elongated body portion and a head portion, wherein the elongated body portion is configured to be secured to a shaft region of the distal femur, wherein the head portion is wider than the body portion and configured to be secured to an end region of the distal femur, and wherein the main plate has a proximal end, a distal end, and a pair of longitudinal edges opposite one another on the main plate and each extending from the proximal end to the distal end of the main plate; (B) a coupling member; and (C) an outrigger plate that is shorter, narrower, and thinner than the main plate, the outrigger plate having a mounting region and an arm, the mounting region being configured to be mounted on the head portion with the coupling member at a rotational position selected from two or more permitted rotational positions of the mounting region, such that that the outrigger plate extends past one of the longitudinal edges of the main plate, wherein the arm defines a plurality of apertures and is configured to be secured to the condylar fragment with fasteners received in the plurality of apertures such that the outrigger plate spans and stabilizes the Hoffa fracture.

Paragraph 22. The system of paragraph 21, wherein mounting region of the outrigger plate includes a loop, and wherein the main plate and the outrigger plate collectively form an interface that permits the loop to be mounted at only a finite series of predefined rotational positions of the loop with respective to the main plate.

Paragraph 23. The system of paragraph 21 or paragraph 22, wherein the coupling member has an external thread that is complementary to an internal thread formed in each of a plurality of apertures defined by the head portion of the main plate.

Paragraph 24. The system of any one of paragraphs 21 to 23, wherein the head portion of the main plate defines a plurality of apertures configured to receive bone screws, and wherein the outrigger plate defines an aperture configured to be mounted coaxial to a first aperture of the plurality of apertures of the head portion, and wherein the first aperture is configured to be spaced proximally or distally on the distal femur from at least one aperture of the plurality of apertures of the head portion and is configured to be spaced posteriorly on the distal femur from at least one aperture of the plurality of apertures of the head portion.

Paragraph 25. The system of paragraph 24, wherein the plurality of apertures of the head portion have the same diameter as one another.

Paragraph 26. The system of any one of paragraphs 21 to 25, wherein the main plate defines a longitudinal center line that conceptually divides the main plate into a pair of lateral portions each bounded in part by the center line and a different one of the longitudinal edges, and wherein the outrigger plate is configured to overlap only one of the lateral portions when mounted to the main plate.

Paragraph 27. The system of any one of paragraphs 21 to 26, wherein the mounting region is wider than the arm and configured to be clamped between the head portion of the main plate and a flange of the coupling member, to mount the outrigger plate firmly to the head portion of the main plate.

Paragraph 28. The system of any one of paragraphs 21 to 27, wherein the mounting region defines an aperture configured to be aligned coaxially with an aperture of the head portion and to be engaged by the coupling member, and wherein the aperture of the mounting region is larger than each aperture of the plurality of apertures of the arm.

Paragraph 29. The system of any one of paragraphs 21 to 28, further comprising a fixation device configured to span the Hoffa fracture independently of the main plate and the outrigger plate, without entering any aperture of either plate.

Paragraph 30. The system of paragraph 29, wherein the fixation device includes a threaded fastener configured to extend into the distal femur from an anterior side thereof and across the Hoffa fracture.

Paragraph 31. The system of paragraph 29 or paragraph 30, wherein the fixation device includes a plate configured to span the Hoffa fracture.

Paragraph 32. The system of any one of paragraphs 21 to 31, wherein the outrigger plate has a curved centerline in an orthogonal projection of the outrigger plate onto a plane parallel to the mounting region.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically state.

We claim:

1. A method of fixing a distal femur having a Hoffa fracture creating a condylar fragment, the method comprising, in any order:
securing a main plate having an elongated body portion and a head portion to the distal femur, wherein the elongated body portion is secured to a shaft region of the distal femur, and wherein the head portion is wider than the body portion and is secured to an end region of the distal femur;
selecting an orientation for an outrigger plate from two or more orientations permitted by an interface between the main plate and the outrigger plate;
mounting the outrigger plate firmly on the head portion of the main plate at the selected orientation with a coupling member, wherein the coupling member is disposed in threaded engagement with a first aperture defined by the head portion of the main plate and extends through a second aperture defined by the outrigger plate; and
fastening an arm of the outrigger plate to the condylar fragment with one or more fasteners such that the outrigger plate spans and stabilizes the Hoffa fracture;
wherein an upper surface of the head portion of the main plate defines a series of first surface features of the interface arranged along a circumferential edge of the first aperture defined by the head portion, wherein a lower surface of the outrigger plate defines a series of second surface features of the interface arranged along a circumferential edge of the second aperture defined by the outrigger plate, and wherein each first surface feature is complementary to each second surface feature.

2. The method of claim 1, wherein the outrigger plate is substantially shorter, narrower, and thinner than the main plate.

3. The method of claim 1, wherein the step of selecting an orientation for an outrigger plate includes a step of selecting an orientation from only a finite series of discrete orientations in which a plurality of the first surface features fit together with a plurality of the second surface features.

4. The method of claim 3, wherein the step of mounting the outrigger plate includes a step of clamping a loop of the outrigger plate between the head portion of the main plate and a flange of the coupling member.

5. The method of claim 1, wherein the step of securing a main plate is performed with bone screws, and wherein the step of fastening an arm of the outrigger plate is performed with bone screws that are smaller in diameter than the bone screws used for the step of securing a main plate.

6. The method of claim 1, further comprising a step of attaching a fixation device to the distal femur such that the fixation device spans the Hoffa fracture independently of the main plate and the outrigger plate and does not enter any aperture of the main plate and does not enter any aperture of the outrigger plate.

7. The method of claim 6, wherein the step of attaching a fixation device includes a step of placing a threaded fastener into the distal femur from an anterior side thereof and across the Hoffa fracture.

8. The method of claim 6, wherein the main plate and the outrigger plate are a first plate and a second plate, and wherein the step of attaching a fixation device includes a step of attaching a third plate to the distal femur such that the third plate spans and stabilizes the Hoffa fracture.

9. The method of claim 1, wherein the coupling member has an external thread that is complementary to an internal thread formed in each of a plurality of apertures defined by the head portion of the main plate.

10. The method of claim 1, wherein the head portion of the main plate defines a plurality of apertures including the first aperture and configured to receive bone screws, wherein the plurality of apertures defined by the head portion have the same diameter as one another, and wherein the first aperture is spaced proximally or distally on the distal femur from at least one other aperture of the plurality of apertures and is spaced posteriorly on the distal femur from at least one other aperture of the plurality of apertures.

11. A method of fixing a distal femur having a Hoffa fracture creating a condylar fragment, the method comprising, in any order:
securing a main plate having an elongated body portion and a head portion to the distal femur, wherein the elongated body portion is secured to a shaft region of the distal femur, and wherein the head portion is wider than the body portion and is secured to an end region of the distal femur;
clamping a mounting region of an outrigger plate between the head portion of the main plate and a flange of a coupling member at a rotational position selected from two or more permitted rotational positions of the mounting region, wherein the outrigger plate is shorter, narrower, and thinner than the main plate, and wherein the coupling member is disposed in threaded engagement with a first aperture defined by the head portion of the main plate and extends through a second aperture defined by the mounting region of the outrigger plate; and
fastening an arm of the outrigger plate to the condylar fragment with one or more fasteners such that the outrigger plate spans and stabilizes the Hoffa fracture, wherein the arm is narrower than the mounting region;
wherein an upper surface of the head portion of the main plate defines a series of first surface features arranged along a circumferential edge of the first aperture defined by the head portion, wherein a lower surface of the mounting region of the outrigger plate defines a series of second surface features arranged along a circumferential edge of the second aperture defined by the mounting region, and wherein a plurality of the first surface features fit together with a plurality of the second surface features in each of the two or more permitted rotational positions of the mounting region.

12. The method of claim 11, further comprising a step of attaching a fixation device to the distal femur such that the fixation device spans the Hoffa fracture independently of the main plate and the outrigger plate and does not enter any aperture of the main plate and does not enter any aperture of the outrigger plate.

13. The method of claim 12, wherein the step of attaching a fixation device includes a step of placing a threaded fastener into the distal femur from an anterior side thereof.

14. The method of claim 12, wherein the main plate and the outrigger plate are a first plate and a second plate, and wherein the step of attaching a fixation device includes a step of attaching a third plate to the distal femur such that the third plate spans and stabilizes the Hoffa fracture.

15. The method of claim 11, wherein the coupling member is a set screw having an external thread that is complementary to an internal thread formed in each of a plurality of apertures defined by the head portion of the main plate.

16. The method of claim 11, wherein the head portion of the main plate defines a plurality of apertures including the first aperture and configured to receive bone screws, wherein the step of clamping includes a step of mounting the second aperture of the outrigger plate coaxial to the first aperture of the plurality of apertures defined by the head portion of the main plate, and wherein the first aperture is spaced proximally or distally on the distal femur from at least one other aperture of the plurality of apertures and posteriorly on the distal femur from at least one other aperture of the plurality of apertures.

17. The method of claim 16, wherein each aperture of the plurality of apertures defined by the head portion of the main plate has an internal thread of the same diameter.

* * * * *